(12) United States Patent
Wang et al.

(10) Patent No.: US 7,648,711 B2
(45) Date of Patent: Jan. 19, 2010

(54) DIMETHICONE-CONTAINING SUSTAINED RELEASE INJECTION FORMULATION

(76) Inventors: Yuwan Wang, 3-506, Building 15, 3 Yuanmingyuan West Road, Haidian District, Beijing (CN) 100094; Zhende Pan, 2 Yuanmingyuan West Road, Haidian District, Beijing (CN) 100094; Xiaoxi Dai, 2 Yuanmingyuan West Road, Haidian District, Beijing (CN) 100094

( * ) Notice: Subject to any disclaimer, the term of this patent is extended or adjusted under 35 U.S.C. 154(b) by 346 days.

(21) Appl. No.: 10/558,151

(22) PCT Filed: Oct. 8, 2003

(86) PCT No.: PCT/CN03/00849

§ 371 (c)(1),
(2), (4) Date: Nov. 25, 2005

(87) PCT Pub. No.: WO2004/103343

PCT Pub. Date: Dec. 2, 2004

(65) Prior Publication Data

US 2007/0053943 A1     Mar. 8, 2007

(30) Foreign Application Priority Data

May 25, 2003   (CN)   ................ 03 1 38019
Jun. 16, 2003   (CN)   ................ 03 1 48883
Aug. 18, 2003  (CN)   ................ 03 1 53569
Sep. 11, 2003  (CN)   ................ 03 1 56876

(51) Int. Cl.
*A01N 25/00*   (2006.01)
*A01N 43/02*   (2006.01)
*A01N 43/04*   (2006.01)
*A01N 43/16*   (2006.01)
*A01N 55/00*   (2006.01)
*A61K 31/70*   (2006.01)
*A61K 31/225*  (2006.01)
*A61K 31/335*  (2006.01)
*A61K 31/35*   (2006.01)
*A61K 31/695*  (2006.01)
*A61F 13/00*   (2006.01)
*A61F 2/00*    (2006.01)

(52) U.S. Cl. ................ 424/405; 424/422; 424/424; 424/426; 514/30; 514/63; 514/450; 514/453; 514/547

(58) Field of Classification Search ............. 424/405
See application file for complete search history.

(56) References Cited

U.S. PATENT DOCUMENTS 5,385,738 A * 1/1995 Yamahira et al. .......... 424/489
2006/0100165 A1 * 5/2006 Manetta et al. ............. 514/28

FOREIGN PATENT DOCUMENTS

EP      0 535 734 A1 * 4/1993

OTHER PUBLICATIONS

Lo PK, Fink DW, Williams JB, and Blodinger J, "Pharmacokinetic studies of ivermectin: effects of formulation." Veterinary Research Communications, 1985, 9(4): 251-68.*
Tenox Antioxidant, retrieved from the internet at http://findarticles.com/p/articles/mi_m3289/is_2_172/ai_97728682 on Mar. 19, 2008, 1 page.*
M. C. Allwood, "Antimicrobial Agents in Single- and Multi-dose Injections", Journal of Applied Bacteriology, 1978, 44, Svii-Sxvii.*

* cited by examiner

*Primary Examiner*—Johann R Richter
*Assistant Examiner*—Nathan W Schlientz
(74) *Attorney, Agent, or Firm*—George G. Wang; Bei & Ocean

(57) ABSTRACT

A sustained release formulation by using dimeticone as the dispersion medium, which includes active ingredient (e.g., drugs against parasites, insecticides, NSAIDs, antibiotics, sex hormone like agents or oily soluble vitamins) and dimeticone as the medium. Suitable stabilizer, antioxidant, local analgesics and material for sustained release may be added. The formulation is bio-compatible, stable and injectable.

2 Claims, No Drawings

DIMETHICONE-CONTAINING SUSTAINED RELEASE INJECTION FORMULATION

FIELD OF THE INVENTION

The present invention relates to a sustained release formulation (long-lasting formulation) suitable for drugs including parasiticides, nonsterioidal anti-inflammatory (NSAIDs), sex hormone agents and antibiotics. This dimethicone-based injection formulation is bio-compatible, stable and easy for injection, and provides satisfactory sustained release action.

CROSS REFERENCE TO RELATED APPLICATIONS/TECHNICAL BACKGROUND INFORMATION

Preparation of long-lasting action injection formulation comprising avermectins with dimethicone as medium was described in Chinese Patent Applications Nos. CN03138019.0 and CN03156876.9. Preparation of long-lasting action veterinary formulation comprising N-phenyl pyrozle agents against parasites (e.g. fipronil) with dimethicone as medium was described in Chinese Patent Application No. CN03148883.8. In addition, preparation of long-lasting action formulation comprising NSAIDs was described in Chinese Patent Application No. CN03153569.0. Furthermore, our recent research suggested that formulation comprising triazine anticoccidial drugs, halofuginone anticoccidial drugs, imidacloprid, diflubenzuron, ceftiofur or sex hormone agents, which is prepared with dimethicone as medium, is stable and easy for injection and can provide satisfactory sustained action and cause little tissue damages. At the same time, it is stable and injectable. Therefore, the present invention includes the subject matters disclosed in our prior Chinese Patent Application Nos. CN03138019.0, CN03156876.9, CN03148883.8 and CN03153569.0, and also includes dimethicone-based preparation of long-lasting action injection formulation used for drugs such as anticoccidial drugs, sex hormone agents, imidacloprid, etc.

Dimethicone, also known as silicone oil, consists of a series of dimethylsiloxane polymers with various viscosities (see Zheng Junmin, *Polymer Science for Pharmaceuticals*, China Medical and Pharmaceutical Technology Press, August 2000, 1 Edition, pp 169-170). It is an oily liquid, highly hydrophobic and physiologically inert. Its viscosity changes little within the application temperature range (from −40° C. to 50° C.). Dimethicone is highly resistant to oxidation and can withstand sterilization at 150° C. for an hour. It is non-reactive to most compounds and very stable when mixed with any chemicals and drugs described in the present invention. The drugs and suspension agents (e.g. hydrogenated castor oil) described in the present invention are substantially insoluble and do not swell in dimethicone. These features are an important basis for dimethicone to be used to prepare the injection formulation of the present invention.

The experiments performed in the present invention suggested that: (1) subcutaneous injection of dimethicone at a dose between 4 ml to 6 ml per injection site per time to subjects (e.g. bovine and caprine) caused no side effect such as obvious tissue damage, swelling, agglomeration, granuloma, etc. Thus, from the view point of bio-compatibility, dimethicone is suitable to be used as medium to prepare formulation for subcutaneous injection. (2) Therapeutic drugs, for example avermectins, N-Phenyl pyrazoles against parasites, triazine anticoccidial drugs, imidacloprid, diflubenzuron, sex hormones, NSAIDs and ceftiofur, penicillin G potassium salt or penicillin G sodium salt, are almost insoluble in dimethicone (solubility less than 0.01%). Therefore, this will not pose any stability problem when using silicone as medium to prepare suspensions comprising the aforesaid drugs, which is one of the important factors usually affecting the sustained action of a long-lasting formulation. (3) Hydrogenated castor oil does not dissolve or swell in silicone oil, and therefore the combination of silicone oil and hydrogenated castor oil can be used as medium to prepare liquid suspensions. When hydrogenated castor oil used within the proper range (0.2% to 0.5%), the resulting liquid suspension is better in terms of stability, fluidity, injectability and long-lasting releasing effect than the injection formulation prepared using water, vegetable oil or other organic liquid as the suspension medium. Hydrogenated castor oil functions as a suspending agent and enhances the effect of sustained releasing. In addition, when the formulation of the present invention is prepared by the micro powder crystallizing method, the presence of hydrogenated castor oil suppresses the growth of the crystal nucleus of active ingredients, whereby producing micro powder of active ingredients with a particle size of 20 micrometers or smaller. (4) By mixing the active ingredients with hydrogenated castor oil or with the-combination of hydrogenated castor oil and ethylcellulose to produce solid dispersion micro powder with particle size smaller than 300 micrometers, then dispersing the micro powder in silicone oil and grinding with a colloid mill or a ball mill, a long lasting release formulation containing solid dispersion of various particle sizes (from 10 micrometer to 150 micrometers) can be produced. Further, the sustained releasing effect of the formulation may be modified by adjusting the particle size of the solid dispersion and the proportion of hydrogenated castor oil relative to the active ingredients. For instance, sustained release formulations with various durations of effectiveness may be prepared as follows: mixing avermectins with hydrogenated castor oil to produce two solid dispersions with the avermectins to hydrogenated castor oil equal to 1:2 and 2:1, respectively, then mixing the two solid dispersions at a given ratio and dispersing the mixture in silicone oil, and producing the solid dispersion in the system with the particle size varying between 85 micrometers to 120 micrometers by controlling the extent of grinding. The formulation can provide an effective sustained releasing period up to 140 days following a single administration. Furthermore, the injection prepared by the above method has better injectability, stability and biocompatibility than water or vegetable oil based sustained release formulations for solid dispersion micro powder of avermectins/hydrogenated castor oil. Specifically, the formulation using water as medium has three disadvantages. First, it has difficulty to maintain an effective sustained releasing for more than 80 days. Second, it has poor injectability and, without adding more water soluble suspension assisting agents, solid suspension phase may "separate" from the water phase, causing injection failure due to blocking of the syringe needle. Third, it results in tissue lumps around the injection site. Other organic liquid based long-lasting formulations have similar problems. Therefore, all previous long-lasting injection formation have proved to have little or no commercial value.

Avermectins suitable for practicing the present invention include, but not limited to, abamectin, ivermectin, emamectin, eprinomectin, doramectin, moxidectin, 4"-O-carbamyl-methyl-abamectin B1 and other avermectin derivatives. The avermectins and avermectin derivatives were described in detail in Chinese Patent Application CN 1345327A (WO00/58328). Structurally, avermectins bear the common structure of macrolide and for this reason they are also called macrolides. The avermectins are highly effective in ridding of or killing those parasites widespread among animals, for example, internal parasites such as nematodes and external parasites such as mite, tick, louse and maggot. Administration of currently available commercial drugs at a dose of 0.2 mg to 0.4 mg/kg bodyweight can repel more than 95% of the parasites, and the action can continue 10 to 20 days. High effectiveness is an important biological basis for the avermectins to be prepared in long-lasting action formulations.

Avermectins are highly hydrophobic and hardly dissolvable in silicone oil, which is an important chemical basis for the avermectins to be prepared in long-lasting action formulations.

However, avermectins do not have the ability to kill parasite eggs. The life cycle for parasites like itch mite, vampire louse, etc. growing from eggs to adults is about 20 days. Therefore, in order to prevent and treat the problems caused by the parasites, two or more administrations of the drug are needed when using in conventional injection or oral formulations. In addition, the parasites like nematodes are widespread in the environment and have the opportunity to infect animals repeatedly. Sustained releasing formulation can prevent animals from be infected by those parasites for a long period with a single administration. Therefore, the situation has created a need for developing long-lasting action or sustained releasing formulations for avermectins.

According to the present invention, avermectins may present in the formulation in the form of fine particles (smaller than 100 micrometers) or in the form of carrier particles. The carrier particles refer to solid dispersion particles, micro-balls, microcapsules, liposome in the solid state, or nano-particles, which are made of avermectins and carrier material for sustained release. The carrier material for sustained release may be hydrogenated castor oil, ethylcellulose, polyesters, polyethylene glycol (PEG) and polyvinyl pyrrolidone (PVP), etc., which may be used alone or in combination. For example, to practice the present invention the carrier material for forming solid dispersion with avermectins may be selected from of the following: hydrogenated castor oil, the combination of hydrogenated castor oil and ethylcellulose, the combination of hydrogenated castor oil, ethylcellulose and polyvinyl pyrrolidone, the combination of ethylcellulose and polyvinyl pyrrolidone, the combination of hydrogenated castor oil and polyvinyl pyrrolidone, the combination of ethylcellulose and polyethylene glycol, the combination of hydrogenated castor oil and polyethylene glycol, or the combination of ethylcellulose and polyethylene glycol. The fast release action or sustained release action of the formulation may be controlled by adjusting the ratio between water-soluble carrier (e.g. PVP and PEG) and hydrophobic carrier (e.g. hydrogenated castor oil and ethylcellulose). The carrier material for sustained release used in the present invention should not dissolve or swell in dimethicone, which is an important basis to ensure the carrier particles' stability and the sustained releasing effect of the formulation.

Experiments suggested that avermectins ground by the air-blow method is difficult to achieve desired particle size. Additionally, this grinding method is energy-consuming, prone to dust contamination and difficult to maintain sterilized processing. Thus, for the present invention it is preferred that the micro powder crystallization method be used to produce fine power of avermectins. The following further details this method: through heating, dissolving and melting avermectins and hydrogenated castor oil in organic solvent with a low boiling point, such as, for example, ethanol, acetic ether and methylene trichloride and then, upon cooling of the solution, adding dimethicone with stirring so that avermectins will precipitate in micro crystal form. Or, alternatively, dispersing avermectins in a small amount of dimethicone to make a viscous liquid, grinding in wet condition (e.g. grinding with a ball mill or a colloid mill), and adding more medium (dimethicone) to the final volume. In addition, it can be made by a method comprising the following steps: producing solid dispersion with avermectins and carrier material (e.g. hydrogenated castor oil), grinding the solid dispersion to micro powder, and dispersing the powder in dimethicone to obtain an injection preparation of the present invention.

The long-lasting action formulation of the present invention, when administered at the dose of 1 to 3 mg of abamectin agents per kilogram of bodyweight, can maintain the drug effectiveness up to 60 to 120 days or longer after a single administration. The effective duration can be modified by adjusting the dosage.

The N-Phenyl pyrazole agents used in the present invention, for example, fipronil, are highly active synthetic chemical insecticides. They have been widely used in agriculture for killing noxious insects. They are also used in the prevention and treatment of problems caused by external parasites, especially fleas and ticks. The preparation methods, formulations and application of fipronil, were described in detail in Chinese Patent CN1018733B. The commercial products of fipronil, such as those in casting formulation and spray, are mainly used to repel and kill flea on cats and dogs and boophilus on cattle. According to the present invention, the sustained release formulation of fipronil was prepared with dimethicone and hydrogenated castor oil as the medium, for repelling and killing flea and boophilus. Subcutaneous injection of this formulation, the effect may be maintained for 3 to 6 months or longer following a single administration.

The Nonsteroidal Anti-inflammatory Drugs (abbreviated as NSAIDs) used in the present invention have the effects of fever reducing, pain relieving and anti-inflammatory, as has been described in detail in some of the pharmaceutical books and manuals (e.g. Ni Wenji, Li Anliang, Pharmaceutical Chemistry, Higher Education Press, 1999, pp 348-375). NSAIDs include the antipyreitc and analgesics category and anti-inflammatory category. The latter includes, for example, salicylates, pyrazolones, aryl alkanoic acids, fenamic acids, benzothiazines etc. NSAIDs' effect is based on inhibition of the prostaglandin synthesis via the cyclooxygenase enzymes (COX). Therefore, other water insoluble COX-2 inhibitors are contemplated in the present invention as well. Water insoluble and slightly water soluble NSAIDs as well as NSAIDs that can be converted to water insoluble through chemical modification are suitable to application of the present invention. The Preferred NSAIDs for practicing the present invention includes indomethacin, ketoprofen, flunixin, diclofenac and piroxican etc. The sustained release formulation of NSAIDs is prepared with silicone oil and hydrogenated castor oil as the carrier material for sustained release. The formulation prepared accordingly is stable, biocompatible, injectable and with good sustained release effect. It is suitable for subcutaneous injection to animals.

5. The compound Imidacloprid used in the present invention has been widely used in the prevention and treatment of problems caused by noxious insects in agriculture. In the veterinary field, they are mainly used for external parasites on cats and dogs. The existing commercial products are of casting formulation and, when administered through skin at the dose of 10 mg/kg body weight, can maintain effectiveness up to about 1 month after a single administration. In contrast, in the sustained release formulation of the present invention, when administered by subcutaneous injection at the dose of 10-100 mg/kg body weight, it can maintain effectiveness up to 80 to 360 days after a single administration. The compound diflubenzuron used in the present invention is a benzy phenylthiourea insecticide and can inhibit the synthesis of chitin in insects, making the larva unable to form new epidermis, which leads to death. Diflubenzuron had been widely used in agriculture in dealing with noxious insects. Outside China, it has been prepared in liquid formulation used in bathwater for getting rid of or killing lice infecting the sheep. In the present invention, diflubenzuron is prepared in a dimethicone based injection formuation for repelling and killing external parasites, such as, louse and flea. It can provide long-lasting action up to 2 to 4 months. The present invention also suitable for the following compounds: triflumuron, cyromazine, estrogen, progesterone, androgen, triazine anticoccidial drugs (e.g. toltrazuril and dliclazuril), cephalosporins (e.g. ceftiofur hydrochloride, ceftiofur sodium and ceftiofur free acid) and other antibiotics. Those compounds are known and commercially available. According to the present invention, they may be prepared in the sustained release formulation with silicone oil, silicone oil/hydrogenated castor oil or silicone oil/hydrogenated castor oil/ethylcellulose.

SUMMARY OF THE INVENTION

The present invention provides a method for preparing a long-lasting sustained release formulation by using dimethicone as dispersing medium. The formulation comprises therapeutic drugs (or active ingredients) 0.5-40% (W/V), dimethicone as the medium. Suitable adjuvant such as non-ionic surfactant, suspending agent, material for sustained release, antioxidant and local analgesics can also be added.

Suitable therapeutic drugs or active ingredients for practicing the present invention are listed as examples in the following:

(1) Avermectins including abamectin, ivermectin, emamectin, eprinomectin, doramectin, moxidectin, 4"-O-carbamylmethyl-abamectin B1 and other abamectin derivatives. Avermectins and Avermectin derivatives were described in detail in Chinese Patent Application No. CN 1345327A (WO00/58328).

(2) NSAIDs including salicylates, pyrazolones, p-aminophenol derivatives, indole, indan acetic acid, aryl alkanoic acids (e.g. mixed aryl acetic acids, and arylpropionic acid), 1,2-benzothiazin, fenamic acids (e.g. enol acids, alkyl ketone), anthranilic acids (belonging to fenamic acids) and other COX-2 inhibitors. Among them, indomethacin, ketoprofen, flunixin, diclofenac and piroxican are preferred.

(3) Antiparasitics, including imidacloprid, diflubenzuron, lufenuron, methoprene, fipronil, trichloropyridin, cyromazine, triazine anticoccidial drugs (e.g. toltrazuril and dliclazuril), albendazole, albendazole sulfoxide hydrochloride, closantel or closantel sodium.

(4) Antibiotics, including cephalosporins, penicillins, β-lactamase inhibitors, thiamuline, tiamulin fumarate, tylosins (e.g. tilmicosin, acetyl isovaleryl tylosin), doxycycline, doxycycline hydrochloride, minocucline, gentamycin, lincomycin, clindamycin, neomycin, polymyxin, quinolones, sulfanilamide, which can be used alone or in combination in the formulation.

(5) Sex hormones, including estrogen, progesterone and androgen.

(6) Oil soluble vitamins.

(7) Mineral elements insoluble in water or slightly soluble in water.

The non-ionic surfactants, suspending agent, material for sustained release includes: glycerol fatty acid esters, polyglycerol fatty acid esters, sugar ester, sorbitan fatty acid esters (Span), polyoxyethylene sorbitan fatty acid esters (Tween), Myrjs, Brijs,Paregal, OP, polyvinyl chloride castor oil, condensation compound, polyvinyl chloride hydrogenated castor oil, condensation compound, Pluronic, fatty acid esters which exists in the form of solid at the temperature below 40° C. (e.g. glycerol monostearate, hydrogenated castor oil and carnauba wax ect.), lanolin, stearic acid, cetyl acohil, poly vinyl pyrrolidone (PVP), polyethylene glycol (PEG) with MW lager than 1000, gelatin, gum Arabic, ethylcellulose, polyvinyl butyral. Particularly preferred stabilizer and material for sustained release thereof comprises Tween, Span, ethylcellulose, hydrogenated castor oil, aluminium stearic acid, PVP and PEG (MW lager than 1000), which can be used alone or in combination.

Suitable antioxidants are oil soluble, with a concentration between 0.01 and 0.5% (W/V) in the formulation. Preferred antioxidant are butylated hydroxytoluene(BHT), butylated hydroxyanisole(BHA), and propyl gallate(PG), which can be used alone or in combination.

Suitable local analgesics includes, but not limited to trichlorobutanol, benzyl alcohol, procaine, tetracaine and lidocaine.

As one embodiment of the present invention, there is provided a sustained release formulation comprising (a) abamectin agents 0.5-30% (W/V), (b) dimethicone to the final volume as the medium, and (c) other additives, such as stablizer, antioxidant and/or local analgesics. A preferred formulation comprises abamectin agents 1-10% (W/V), hydrogenated castor oil 0-10% (W/V), dimethicone with viscosity less than 100 mm2/S to the final volume as the medium. One or more antioxidanst and local analgesics can also be added. The following are preferred methods of preparing the formulation:

Method (1): to a certain amount of avermectins adding alcohol (2-5 times the amount of avermectins), acetone or another organic solvent with a low boiling point, with or without adding hydrogenated castor oil added; dissolving/melting the drug at the temperature of 85° C.; let it cooling while stirring; then adding dimethicone to the final volume; removing alcohol, acetone or other organic solvent by lowering the pressure; and thereafter homogenizing (e.g. by colloid mill or ball mill) to obtain a sustained release formulation.

Method (2): a certain amount of avermectins, adding a small amount of dimethicone and hydrogenated castor oil; melting hydrogenated castor oil at the temperature of 90° C.; cooling with stirring to produce a paste-like viscous liquid; grinding (with a colloid mill or a ball mill) to the particle size of 100 micrometers, and then adding more dimethicone to the final volume.

Method (3): Dispersing the micro powder of avermectins (particle size smaller than 100 micrometers) to melted hydrogenated castor oil; adding dimethicone; homogenizing; and thereafter adding more dimethicone to the final volume.

Method (4): Dispersing the solid dispersion comprising avermectins and hydrogenated castor oil in dimethicone; heating with stirring at a temperature around 90° C.; When the mixture is melted, let it cooling and continue stirring until the mixture is homogenized; and thereafter adding more dimethicone to the final volume.

Method (5): Dispersing the solid dispersion comprising avermectins and hydrogenated castor oil in dimethicone; grinding (with colloid mill or ball mill); homogenizing; and upon the particle size reaching smaller than 120 micrometers, adding more dimethicone to the final volume.

A preferred formulation and preparation method are provided in the following.

(1) Composition of the Formulation:

| | |
|---|---|
| a. Avermectins-carrier powder | 2-35% (W/V) |
| b. Suspending agents (e.g. hydrogenated castor oil) | 0-3% (W/V) |
| c. local analgesics | 0.5-2.5% (W/V) |
| d. dimethicone | to the final volume |

(2) Method of Preparing the Formulation:

Disperse avermectins-carrier powder (particle size less than 360 micrometer) in dimethicone; grind until the particle size becoming smaller than 150 micrometers; then add and mix with dimethicone (with or without suspending agent therein) to the final volume. Or, Disperse avermectins-carrier powder (particle size less than 120 micrometer) in a sufficient amount of dimethicone with or without suspending agent therein; and then homogenize to obtain the final product.

The above described Avermectins-carrier powder is a solid dispersion comprising avermectins and carrier material for sustained release or another kind of carrier powder (e.g. microball, microcapsule or nanoparticle).

The carrier material for sustained release can be hydrophilic or hydrophobic. Preferred hydrophilic material may be gelatin, gum Arabic, PEG (MW lager than 1000) or PVP. Preferred hydrophobic material may be ethylcellulose, polyvinylbutyral, or hydrogenated vegetable oil (e.g. hydrogenated castor oil). More preferred hydrophobic material is ethylcellulose, hydrogenated castor oil, PEG (MW lager than 1000), and PVP, which can be used alone or in combination.

The long-lasting action formulation of avermectins according to the present invention is suitable for the prevention and treatment of problems caused by parasites in animals. It is preferred by subcutaneous injection, preferably at the site of the skin behind the ear, or on the neck or back. A possible dose range is 0.2-6 mg/kg (active ingredient/body weight), preferably 1-3 mg/kg. A single administration can provide useful effect up to 40-140 days. The sustained release period can be modified by adjusting the dosage. The adjustment can be conducted by people with ordinary skill in the art. The formulation does not induce tissue damages at the site of injection such as glomerula or tissue damages.

The sustained release formulation for NSAIDs according to the present invention comprises (a) NSAIDs 1-15% (W/V), (b) hydrogenated castor oil 0-5% (W/V), (c) dimethicone to the final volume, and optionally (d) suitable adjuvant such as antioxidants and local analgesics. The formulation can be prepared by one of the following methods:

Method (1): to a suitable amount of NSAIDs, adding 2-5 times amount of alcohol, acetone or other organic solvent with a low boiling point; adding optional hydrogenated castor oil; dissolving/melting the mixture at around 85° C.; cooling by stirring; adding dimethicone to the final volume; removing alcohol, acetone or other organic solvent by reducing the pressure; and thereafter homogenizing (e.g. by a colloid mill) to obtain the final product.

Method (2): to a certain amount of NSAIDs and hydrogenated castor oil, adding a small amount of dimethicone; melting hydrogenated castor oil at around 90° C.; cooling by stirring to produce a paste-like viscous liquid; grinding (with a colloid mill or a ball mill) until the particle size becoming smaller than 100 micrometers; adding more dimethicone and adjuvant to the final volume.

Method (3): Dispersing a certain amount of micro powder of NSAIDs (particle size smaller than 100micrometers) to melted hydrogenated castor oil; adding dimethicone; homogenizing; and thereafter adding more medium to the final volume.

Method (4): Dispersing a certain amount of NSAIDs/hydrogenated castor oil solid dispersion in dimethicone; heating with stirring at the temperature of 90° C. or so; upon melting of the mixture, cooling it with stirring until it is homogenized; and then adding more medium and adjuvant to the final volume.

Method (5): Dispersing a certain amount of NSAIDs/hydrogenated castor oil solid dispersion in dimethicone; grinding (with a colloid mill or a ball mill); homogenizing; upon the particle size reaching 120 micrometers, adding more medium and adjuvant to the final volume.

As another aspect of the invention, there is provided sustained release formulation and its preparation for fipronil, diflubenzuron or imidacloprid.

(1) Formulation: (a) fipronil, diflubenzuron or imidacloprid 2-10% (W/V), (b) hydrogenated castor oil 0.2-5% (W/V), (b) dimethicone to the final volume, and optionally, (d) suitable adjuvant such as antioxidant and local analgesics.

(2) Preparation methods: Method (a) to fipronil, diflubenzuron or imidacloprid, adding alcohol, acetone or another organic solvent with a low boiling point; adding hydrogenated castor oil; dissolving/melting the mixture at around 85° C.; cooling with stirring; adding dimethicone to the final volume; removing alcohol, acetone or other organic solvent by reducing pressure; and thereafter homogenizing (e.g. by a colloid mill) to obtain the final products. Method (b): adding a small amount of dimethicone to fipronil, diflubenzuron or imidacloprid and hydrogenated castor oil; melting hydrogenated castor oil at around 90° C.; cooling with stirring to produce a paste-like viscous liquid; grinding (with a colloid mill or a ball mill) until particle size becoming below 100 micrometers; and then adding more medium and adjuvant to the final volume. Method (c): dispersing a certain amount of micro powder of fipronil, diflubenzuron or imidacloprid (fineness less than 100 micrometers) in melted hydrogenated castor oil; adding dimethicone; homogenizing; and then adding more medium to the final volume. Method (d): dispersing in dimethicone a certain amount of solid dispersion of fipronil, diflubenzuron or imidacloprid and hydrogenated castor oil; heating with strring at the temperature around 90° C.; upon melting of the mixture, cooling it with stirring until it is homogenized; and then adding more medium and adjuvant to the final volume. Method (e): dispersing in dimethicone a certain amount of solid dispersion comprising fipronil, diflubenzuron or imidacloprid and hydrogenated castor oil; grinding (with a colloid mill or a ball mill); homogenizing; and when the particle size reduces to smaller than 120 micrometers, adding more medium and adjuvant to the final volume.

As another aspect of the present invention, there is provided a sustained release formulation for penicillin or cephalosporins and methods for preparing thereof.

(1) Formulation: (a) penicillin or cephalosporins 2-40% (W/V), (b)hydrogenated castor oil 0-5% (W/V), (c) dimethicone to the final volume, and optionally (d) suitable adjuvant such as antioxidant and local analgesics.

(2) Preparation Methods: Method (a): adding a small amount of dimethicone to penicillin or cephalosporins to make a paste-like viscous liquid; optionally grinding (with a colloid mill or a ball mill); adding dimethicone that contains melted hydrogenated castor oil; dissolving/melting the mixture at the temperature around 85° C.; cooling it with stirring to make a viscous liquid; grinding (e.g. with a colloid mill or a ball mill) until the particle size reaches 100 micrometers; and adding more medium and adjuvant to the final volume. Method (b): dispersing a certain amount of micro powder of penicillin or cephalosporins (particle size smaller than 100 micrometers) to melted hydrogenated castor oil; adding dimethicone; homogenizing; and then adding the more medium and adjuvant to the final volume. Method (c): adding a small amount of dimethicone to penicillin or cephalosporins to make a viscous liquid; grinding (with a colloid mill or a ball mill) until the particle size reaches 100 micrometers; and then adding more dimethicone and adjuvant to the final volume.

According to the aforesaid preparation methods, it is contemplated that other therapeutic drugs may be prepared in sustained release formulation with dimethicone, dimethicone/hydrogenated castor oil, or dimethicone/hydrogenated castor oil/ethylcellulose as medium. It is within the ordinary skill of the art to apply the methods to other drugs based on the disclosure of the present invention.

DETAILED DESCRIPTION OF PARTICULAR EMBODIMENTS

The following examples are provided to illustrate the present invention. They should not be construed to limit the scope of the invention in any manner whatsoever.

EXAMPLE 1

Preparation of 10% Abamectin Suspension Formulation

To 1 kg of abamectin, add 3-4 liters of alcohol, dissolve Abamectin at 90° C., stir the solution until it cools down, add 5 liters of dimethicone with a viscosity of 100 mm$^2$/S and continually stir the mixture, remove the alcohol by reducing the pressure, grind with a colloid mill, and lastly, add dimethicone containing trichlorobutanol (5% of the final volume) and antioxidant to the final volume, resulting in the final product.

EXAMPLE 2

Preparation of 5% Doramectin Suspension Formulation

To 1 kg of doramectin and 0.3 kg of hydrogenated castor oil, add 5 liters of dimethicone with a viscosity of 20 mm$^2$/S, dissolve doramectin at 90° C., stir and let it cool down to a paste-like liquid, grind it with a colloid mill until the particle size reduces to smaller than 100 micrometers, add dimethicone (containing trichlorobutanol and antioxidant) to the final volume, resulting the final product.

EXAMPLE 3

Preparation of 20% Ivermectin Suspension Formulation

To 2 kg of ivermectin and 0.2 kg of hydrogenated castor oil, add 6 liters of alcohol, dissolve ivermectin at 90° C., stir and at the same time add 8 liters of cooled dimethicone with viscosity of 20 mm$^2$/S while the mixture is cooling down, remove the alcohol by reducing the pressure, grind with a colloid mill to obtain a paste-like formulation.

The formulation is suitable for using on cattle and caprine against parasites by subcutaneous injection behind ears or no the neck with the dosage of 2-3 mg/kg body weight. A single administration (implanting) can have lasting effectiveness up to 120 days or more. Implanting is accomplished by subcutaneous injection with a conventional syringe (using #6 needle). Because there is no need for surgery, it is better than solid implant.

EXAMPLE 4

Preparation of 5% Eprinomectin Long-lasting Formulation

To 14 kg of solid dispersion micro powder (particle size smaller than 300 micrometers) containing 71.4% of eprinomectin and 28.6% (W/W) of hydrogenated castor oil, add 90 liters of dimethicone, mix thoroughly, grind with colloid mill until the particle size of the dispersion reduces to smaller than 100 micrometers, add 100 liters of dimethicone which contains a proper amount of trichlorobutanol and antioxidant, and mixed thoroughly to obtain the final product.

EXAMPLE 5

Preparation of 5% Ivermectin Long-lasting Formulation

To 1 kg of ivermectin and 0.3 kg of hydrogenated castor oil, add 6 liters of alcohol, dissolve ivermectin at 90° C., stir the solution while it cools down, upon solidification, add 9 liters of dimethicone with a viscosity of 20 mm$^2$/S, continue stirring, remove the alcohol by reducing the pressure, grind by a colloid mill, and lastly add dimethicone which contains trichlorobutanol and antioxidant to the final volume to obtain the final product.

EXAMPLE 6

Assay of Drug Concentration in the Blood for the Formulation made in Example 5

The experiment was performed on sheep, which were administered with 1.5 ml of the formulation of Example 5 by subcutaneous injection. Blood samples were collected according to a given schedule and the concentration of ivermectin was assayed by fluorescence-HPLC. Results are shown in the following table:

| Sampling Time (days) | Blood concentration (ng/ml) |
| --- | --- |
| 1 | 7 |
| 2 | 12 |
| 3 | 16 |
| 5 | 18 |
| 7 | 25 |
| 10 | 17 |
| 35 | 11 |
| 50 | 6 |
| 65 | 4 |
| 80 | 2 |
| 95 | 1.1 |

EXAMPLE 7

Preparation of 5% Ivermectin Long-lasting Formulation

To solid dispersion micro powder (particle size smaller than 300 micrometers) containing ivermectin/hydrogenated castor oil (1:2, W/W) and 4.5 kg of solid dispersion micro powder (particle size smaller than 300 micrometers) containing ivermectin/hydrogenated castor oil (2:1, W/W), add 30-50 liters of dimethicone (with a viscosity of 20 mm$^2$/S), grind with a colloid mill or ball mill until the particle size of the solid dispersion reduces to smaller than 90-12 micrometers, and lastly add dimethicone (20 mm$^2$/S) containing a proper amount of trichlorobutanal and antioxidant to the final volume (100 liters).

EXAMPLE 8

Blood Drug Concentration: Formulation of Example 7 vs. 6% Ivermectin Water Suspension The experiment was performed with sheep as subjects, which were divided into three groups with five sheep per group. Group1 were administered with 1.5 ml/50 kg b.w. (1.8 mg of ivermetctin/kg b.w.) of the formulation of Example 7 by subcutaneous injection. Group2 were administered with 1.5 ml (1.8 mg of ivermectin/kg b.w.) of 6% of ivermectin water suspension (which contained 6% of ivermectin, 20% of 1,2-Propylene glycol, 8% of PEG10000, and water as the medium). Group3 were administered with 1.5 ml of 6% of ivermectin water suspension (solid dispersion micro powder comprising 12% of ivermectin/hydrogenated castor oil (1:1), 8% of PEG10000, and water added to 100%). Blood samples were collected according to the schedule and the concentration of ivermectin (ng/ml) was assayed. Results were shown in the following table (values in the table are the average value):

| Sampling Time (days) | Blood concentration (ng/ml) | | |
|---|---|---|---|
| | Group 1 | Group 2 | Group 3 |
| 1 | 5 | 16 | 14 |
| 3 | 11 | 35 | 31 |
| 5 | 14 | 28 | 26 |
| 7 | 22 | 19 | 17 |
| 10 | 22 | 11 | 10 |
| 35 | 15 | 6.7 | 5.1 |
| 50 | 9 | 3.8 | 4.4 |
| 65 | 8 | 2.3 | 3 |
| 80 | 6 | 0.6 | 1.2 |
| 100 | 4 | 0 | 0.3 |
| 120 | 4 | 0 | — |

EXAMPLE 9

Observation of Damages at the Injection Site by the Same Three Types of Formulation used in Example 8

The experiment was performed on yellow cattle as subjects, which were divided into three groups with 10 animals per group and administered with 6 ml of the same drug formulation as used in Group 1, Group 2 and Group 3 of Example 8, respectively. Results: damages such as swelling and granuloma were not observed in Group 1 and Group 2. Agglomeration (3-5 cm in size) occurred in four of the animals in group 3 at the site of injection, which gradually disappeared 20 days later.

EXAMPLE 10

Blood Drug Concentration after Administering the Formulation of Example 7 with Different Administration Dosages The experiment was performed on sheep as subjects, which were divided into two groups with 5 animals per group. Group 1 were administered with 1 ml/50 kg b.w. (1.2 mg of ivermectin/ke b.w.) of the formulation according to Example 7. Group 2 were administered 1.5 ml/50 kg b.w. (1.8 mg of ivermectin/ke b.w.) of the formulation according to Example 7. Blood samples were collected according to the schedule and the concentration of ivermectin (ng/ml) was assayed. Results are shown in the following table:

| Sampling Time (days) | Blood concentration (ng/ml) | |
|---|---|---|
| | Group 1 | Group 2 |
| 3 | 6 | 7 |
| 5 | 11 | 16 |
| 7 | 16 | 18 |
| 10 | 21 | 24 |
| 30 | 14 | 17 |
| 50 | 6 | 11 |
| 70 | 4 | 7 |
| 90 | 1.5 | 4 |
| 110 | 0.6 | 3 |

EXAMPLE 11

Long-lasting Release Formulation for Fipronil (1) Formulation: (a) fipronil 7% (W/V), (b)hydrogenated castor oil 1.5% (W/V), (c) trichlorobutanol 0.5% (W/V), and (d) dimethicone (20mm$^2$/S) to the final volume, i.e., as the medium.

(2) Preparation method: Mix Fipronil with acetone at the ratio of 1:1, heat at around 85° C. until dissolving completely, then mix with melted hydrogenated castor oil, stir at room temperature, upon becoming a semi-solid add 3-4 times amount of dimethicone (20 mm$^2$/S), continue stirring with reduced pressure until all acetone evaporates, grind with a colloid mill, and lastly add trichlorobutanol and dimethicone to the final volume.

EXAMPLE 12

Long-lasting Release Formulation of Fipronil/Hydrogenated Castor Oil Micro Powder (1) Formulation: (a) fipronil/hydrogenated castor oil (1:0.5) solid dispersion micro powder 15% (W/V) and (b) dimethicone (20 mm$^2$/S) to the final volume.

(2) Preparation method: (a) preparing solid dispersion micro powder: mix fipronil with acetone at the ratio of 1:1-1:2, dissolve the solid by heating, then mix with melted hydrogenated castor oil, stir until solidified, dry naturally or under a reduced pressure to remove acetone to obtain a solid dispersion, and grind the solid dispersion until the particle size reduces to smaller than 300 micrometers, resulting in solid dispersion micro powder of fipronil 1/hydrogenated castor oil; (b) preparing sustained release formulation: disperse the above made micro powder in a certain amount of dimethicone, grind with a colloid mill to reduce the particle size to 90-120 micrometers, then add more dimethicone to the final volume.

EXAMPLE 13

Long-lasting Release Formulation for Fipronil (1) Formulation: (a) fipronil micro powder 10% (W/V), (b) hydrogenated castor oil 1.5% (W/V), and (c) dimethicone (20 mm$^2$/S) to the final volume.

(2) Preparation method: disperse fipronil micro powder with particle size smaller than 75 micrometers in dimethicone (of an amount accounting for about 50% of the final volume), stir to make it homogeneously dispersed, add more dimethicone which contains hydrogenated castor oil to the final volume, grind with colloid mill to obtain an homogenized final product.

EXAMPLE 14

Long-lasting Release Formulation for Ketoprofen (1) Formulation: (a) ketoprofen 10% (W/V), (b) hydrogenated castor oil 1.5% (W/V), (c)-trichlorobutanol 0.5% (W/V), and (d) dimethicone (20 mm$^2$/S) to the final volume.

(2) Preparation method: mix ketoprofen with alcohol at the ratio of 1:1, heat at around 40° C. to dissolve the mixture completely, add melted hydrogenated castor oil, mix them thoroughly, stir at room temperature until it becomes semi-solidified, add 3-4 times amount of dimethicone (20 mm$^2$/S), continue stirring at a reduced pressure until the alcohol evaporates, grinded by a colloid mill, and lastly add trichlorobutanol and dimethicone to the final volume.

EXAMPLE 15

Long-lasting Release Formulation Made with Diclofenac Micro Powder (1) Formulation: (a) diclofenac micro powder 10% (W/V), (b) hydrogenated castor oil 2% (W/V), and (c) dimethicone (20 mm$^2$/S) to the final volume as the medium.

(2) Preparation method: disperse diclofenac micro powder (particle size smaller than 75 micrometers) in dimethicone (of a volume accounting for about 50% of the final volume), stir the mixture making it homogeneously dispersed, add more dimethicone containing hydrogenated castor oil to the final volume, and grind with a colloid mill to homogenize it, resulting in the final product.

EXAMPLE 16

Long-lasting Action Formulation Made with Ceftiofur Micro Powder (1) Formulation: (a) ceftiofur micro powder 15% (W/V), (b) hydrogenated castor oil 2% (W/V), (c) trichlorobutanol 0.5% (W/V), and (d) dimethicone (20 mm$^2$/S) to the final volume.

(2) Preparation method: disperse ceftiofur micro powder (particle size smaller than 100 micrometers in dimethicone (of a volume accounting for 50% of the final volume), stir the mixture making it homogeneously dispersed, add more dimethicone containing hydrogenated castor oil and trichlorobutanol to the final volume, and grind with a colloid mill to homogenize it to produce the final product.

EXAMPLE 17

Liquid Formulation of Potassium Penicillin G (1) Formulation: (a) potassium penicillin G 35% (W/V), (b) hydrogenated castor oil 0.5% (W/V), (c) trichlorobutanol 0.5% (W/V), and (d) dimethicone (20 mm$^2$/S) to the final volume.

(2) Preparation method: disperse potassium penicillin G in dimethicone (of a volume accounting for 50% of the final volume), stir the mixture making it homogeneously dispersed, grind with a colloid mill until the particle size reduces to smaller than 150 micrometers, add more dimethicone containing hydrogenated castor oil and trichlorobutanol to bring it to the final volume, and grind with a colloid mill to homogenize it to produce the final product.

EXAMPLE 18

Long-lasting Release Formulation of 5% Ivermectin

To 11 kg of ivermectin, add 4 kg of melted hydrogenated castor oil and 18-22 liters of acetic ether, dissolve the mixture by heating or refluxing, let it cool down rapidly by stirring under a reduced pressure, upon solidification, continue with the low pressure drying to remove acetic ether, add 200 liter of dimethicone (containing 1 kg of trichlorobutanol and 0.2 kg of BHT), stir and heat at around 90° C. to melt the hydrogenated castor oil, cool it down to below 30° C. while stirring, and homogenize (with a colloid mill or a sieve with 100 mesh) to obtain the final product.

EXAMPLE 19

Long-lasting Release Formulation of 14% Albendazole Sulfoxide

To 14 g of albendazole sulfoxide and 1 g of hydrogenated castor oil, add 40 ml of dimethicone, heat the mixture at around 90° C. to melt the hydrogenated castor oil, then stir and cool it down to below 30° C., homogenize, and finally add dimethicone to the final volume.

EXAMPLE 20

Long-lasting Release Formulation of 10% Closantel Sodium

To 13 g of micro powder of closantel sodium/hydrogenated castor oil (10:3, W/W) solid dispersion, add approximately 40 ml of dimethicone (20 mm$^2$/S), grind until the particle size of closantel sodium/hydrogenated castor oil solid dispersion micro powder reduces to 80-130 micrometers, and then add dimethicone to the final volume.

EXAMPLE 21

Long-lasting Release Formulation of 4% Doramectin

To 9 kg of micro powder of doramectin/hydrogenated castor oil/ethylcellulose (1:0.5:0.3, W/W/W) solid dispersion (particle size smaller than 300 micrometers), add 30-50 liters of dimethicone (20 mm²/S), grind the mixture with a colloid mill or a ball mill until the particle size reduces to 70-100 micrometers, and add dimethicone (20 mm²/S) containing trichlorobutanol and antioxidant to the final volume.

EXAMPLE 22

Long-lasting Release Formulation of 3% Ivermectin

To 9 kg of micro powder of ivermectin/hydrogenated castor oil/PVP (1:0.7:0.7, W/W/W) solid dispersion (particle size smaller than 300 micrometers), add 30-50 liters of dimethicone (20 mm²/S), grinded with a colloid mill or a ball mill until the particle size of the solid dispersion reduces to 70-100 micrometers, and add dimethicone (20 mm²/S) containing trichlorobutanol and antioxidant to the final volume.

EXAMPLE 23

Solid Dispersion of Avermectins (Method 1)

To avermectins and hydrogenated castor oil, add alcohol, acetone, acetic ether or another organic solvent with a low boiling point, heat the mixture to dissolve avermectins and melt hydrogenated castor oil, cool it down with constant stirring, upon solidification, reduce the pressure to remove the solvent to obtain a solid dispersion, and grind the solid dispersion to micro powder.

EXAMPLE 24

Solid Dispersion of Avermectins (Method 2)

To avermectins and hydrogenated castor oil, add alcohol, acetone, dimethyl acetamide or dimethylformamide, heat the mixture to dissolve avermectins and melt hydrogenated castor oil, poured the mixture into cool water with constant stirring, upon solidification, filter the mixture, take the solid and dry it naturally or under a reduced pressure to obtain solid dispersion, grind the solid dispersion to micro powder.

EXAMPLE 25

Solid Dispersion of Avermectins (Method 3)

To the mixture of avermectins, hydrogenated castor oil and ethylcellulose, add alcohol, acetone, dimethyl acetamide or N-Methyl pyrrolidone, heat the mixture to dissolve abamectins and ethylcellulose and melt hydrogenated castor oil, pure the mixture into cool water while constantly stirring, upon solidification, filter the mixture, take the solid and dry it naturally or under a reduced pressure to obtain a solid dispersion, grind the solid dispersion to micro powder.

EXAMPLE 26

Solid Dispersion of Avermectins (Method 4)

To the mixture of avermectins, ethylcellulose and hydrogenated castor oil, add acetone, acetic ether or another organic solvent with a low boiling point, heat the mixture to dissolve avermectins and melt ethylcellulose and hydrogenated castor oil, cool it down by stirring, when solidified, dry it naturally or under a reduced pressure to remove solvent, resulting in a solid dispersion, and finally grind the solid dispersion to micro powder.

EXAMPLE 27

Solid Dispersion of Avermectins (Method 5)

To the mixture of avermectins, PVP and hydrogenated castor oil, add alcohol, heat the mixture to dissolve or melt avermectins, PVP and hydrogenated castor oil, cool it down by stirring, when solidified, dry it naturally or under a reduced pressure to remove solvent, resulting in a solid dispersion, and grind the solid dispersion to micro powder.

General knowledge about aseptic technique or the demand of aseptic material is well-known to a person skilled in the art, and therefore is not described in the examples of the present invention. This, however, does not mean that aseptic processing is not required in the preparation of the formulation of the present invention.

We claim:
1. A sustained release injection formulation, comprising
   a. one or more avermectins selected from the group consisting of abamectin, ivermectin, emamectin, eprinomectin, doramectin and moxidectin, and accounting for 0.5-30%, W/V;
   b. hydrogenated castor oil accounting for 1-10%, W/V;
   c. local analgesics accounting for 0.5-3%, W/V;
   d. one or more members selected from the group consisting of butylated hydroxytoluence, butylated hydroxyanisole and propyl gallate, and accounting for 0.2%, W/V; and
   e. dimethicone to the final volume.
2. The sustained release injection formulation of claim 1, wherein
   a. said one or more avermectins accounts for 1-10%, W/V; and
   b. said hydrogenated caster oil accounts for 1-5%, W/V.

* * * * *